United States Patent
Ramer et al.

(10) Patent No.: US 7,345,331 B1
(45) Date of Patent: Mar. 18, 2008

(54) FERROELECTRIC CAPACITOR CIRCUIT FOR SENSING HYDROGEN GAS

(75) Inventors: Orville G. Ramer, Los Angles, CA (US); Stuart C. Billette, Tigard, OR (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 314 days.

(21) Appl. No.: 11/239,459

(22) Filed: Sep. 23, 2005

(51) Int. Cl.
*H01L 29/769* (2006.01)
*H01L 21/00* (2006.01)
*H01L 27/148* (2006.01)

(52) U.S. Cl. .............. 257/296; 257/241; 257/295; 257/E21.664; 257/E23.075; 438/3

(58) Field of Classification Search .......... 257/241, 257/E21.664; 438/3
See application file for complete search history.

(56) References Cited

U.S. PATENT DOCUMENTS

| | | | | |
|---|---|---|---|---|
| 3,621,343 A | * | 11/1971 | Pulvari et al. ............ 361/434 |
| 5,185,130 A | * | 2/1993 | Camanzi et al. ............ 422/90 |
| 5,470,756 A | * | 11/1995 | Coles et al. ............... 436/144 |
| 5,760,433 A | * | 6/1998 | Ramer et al. .............. 257/295 |
| 5,804,823 A | * | 9/1998 | Ramer et al. ........... 250/338.3 |
| 6,203,869 B1 | | 3/2001 | Dougherty et al. ........ 428/35.7 |
| 6,225,156 B1 | * | 5/2001 | Cuchiaro et al. .......... 438/240 |
| 6,275,425 B1 | | 8/2001 | Eliason .................. 365/189.11 |
| 6,693,791 B2 | | 2/2004 | Nakamura .................. 361/302 |
| 7,231,810 B2 | * | 6/2007 | Moritz et al. ............. 73/31.06 |
| 2002/0187583 A1 | * | 12/2002 | Chang et al. ............... 438/49 |
| 2003/0024813 A1 | * | 2/2003 | Taniguchi .................. 204/424 |

\* cited by examiner

*Primary Examiner*—B. William Baumeister
*Assistant Examiner*—Igwe U. Anya
(74) *Attorney, Agent, or Firm*—John Tarlano

(57) ABSTRACT

A ferroelectric capacitor circuit for sensing hydrogen gas having a closed integrated circuit package, a ferroelectric capacitor within the closed integrated circuit package, the ferroelectric capacitor having a bismuth oxide based ferroelectric layer being able to absorb hydrogen gas that is within the closed integrated circuit package, absorbed hydrogen gas chemically reducing a portion of the bismuth oxide based ferroelectric layer into bismuth metal, the ferroelectric capacitor having a ferroelectric voltage, the ferroelectric voltage having a voltage strength, and means for measuring a decrease in the voltage strength of the ferroelectric voltage of the ferroelectric capacitor.

4 Claims, 2 Drawing Sheets

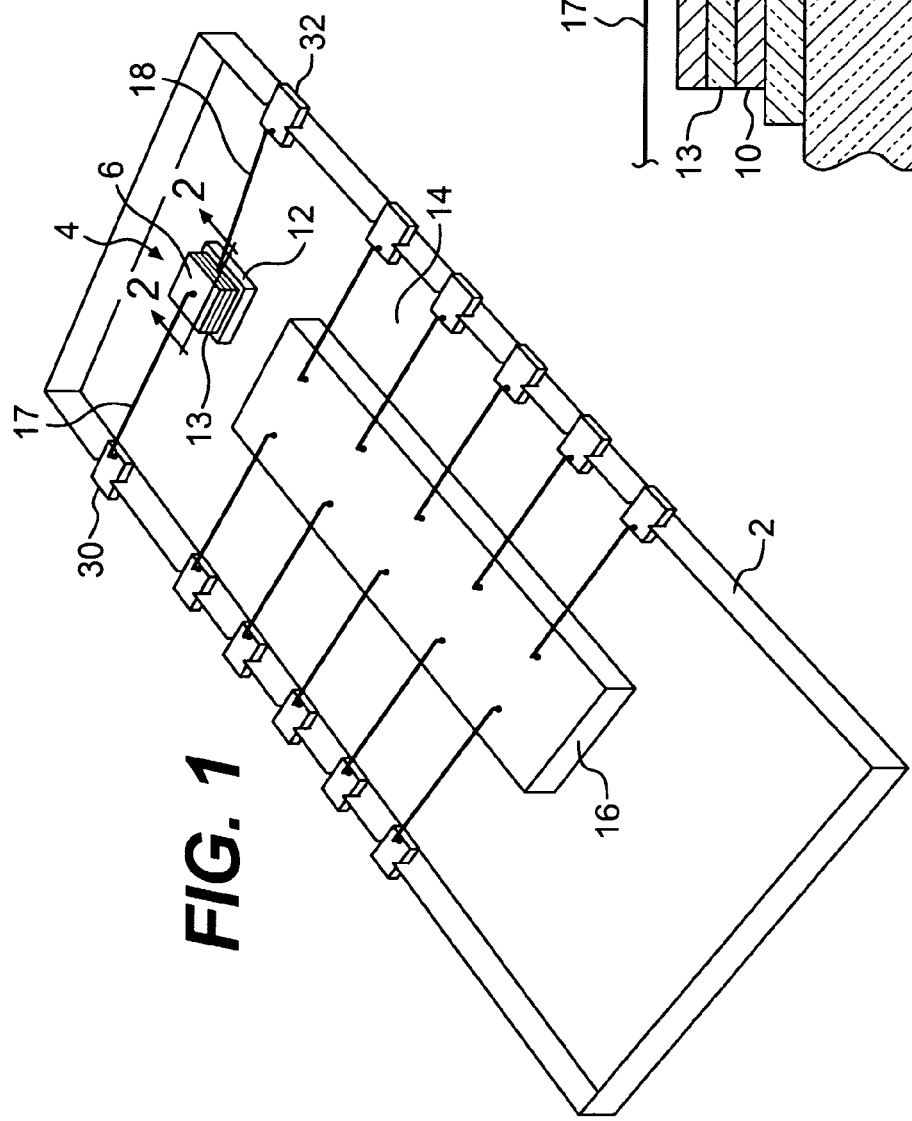
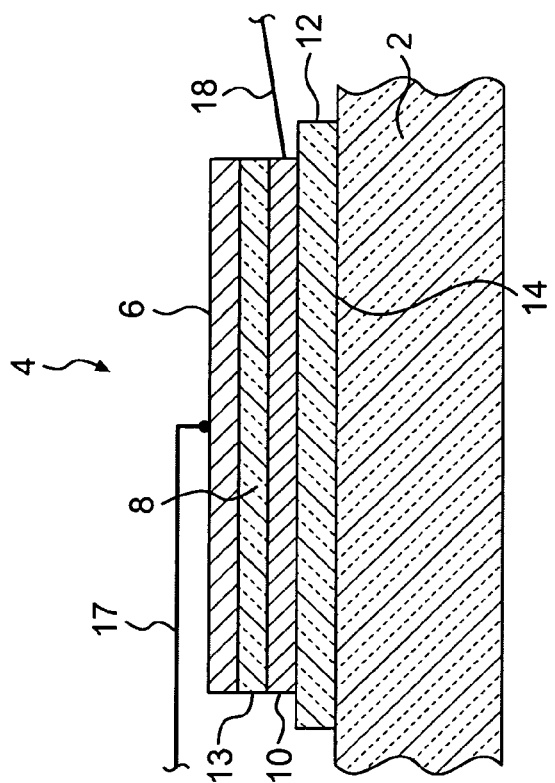
FIG. 1
FIG. 2

FERROELECTRIC CAPACITOR CIRCUIT FOR SENSING HYDROGEN GAS

U.S. Pat. No. 6,203,869 discloses a sealed microelectronic package having a hydrogen gas gettering system. The '869 patent discloses a microelectronic device in the package. However the microelectronic device is not part of a ferroeleric capacitor circuit for sensing hydrogen gas.

The presently disclosed invention is a ferroelectric capacitor circuit for sensing hydrogen gas. The ferroelectric capacitor circuit has a ferroelectric capacitor. The ferroelectric capacitor is given a ferroelectric voltage. The ferroelectric capacitor circuit has an electrometer for sensing voltage strength of the ferroelectric voltage of the ferroelectric capacitor, over time.

The ferroelectric capacitor has an exposed bismuth oxide based ferroelectric layer. The ferroelectric capacitor is placed into an integrated circuit package and the package is closed. The exposed bismuth oxide based ferroelectric layer is energized into a ferroelectric state. Leakage of hydrogen gas into the closed integrated circuit package decreases the voltage strength of the ferroelectric voltage of the bismuth oxide based ferroelectric layer over time. The rate of leakage of hydrogen gas into the integrated circuit package, over time, is indicated on the electrometer of the ferroelectric capacitor circuit. The ferroelectric capacitor is part of the ferroelectric capacitor circuit.

The voltage strength of the ferroelectric voltage of the ferroelectric capacitor decreases over time, as hydrogen gas chemically reduces bismuth oxide of the bismuth oxide based ferroelectric layer into bismuth metal over time. Degradation, over time, of the bismuth oxide based ferroelectric layer by hydrogen gas, occurs in the ferroelectric capacitor. The bismuth metal is not a ferroelectric but is, instead, a conductor. Since there is less ferroelectric material in the ferroelectric capacitor, over time, the voltage strength of the ferroelectric voltage of the ferroelectric capacitor decreases over time.

A closed integrated circuit package, having the ferroelectric capacitor in the package can be heated over time. The heat increases the rate of chemical reduction of the bismuth oxide based ferroelectric layer, by hydrogen gas that leaks into the closed integrated circuit package.

Hydrogen gas, that is absorbed by the bismuth oxide based ferroelectric layer of the ferroelectric capacitor, decreases an ability of the ferroelectric capacitor to maintain a particular voltage strength of the ferroelectric voltage. A change in voltage strength of the ferroelectric voltage of the ferroelectric capacitor is measured by the ferroelectric capacitor circuit. Measurements are made of the amount of change in the voltage strength of the ferroelectric voltage of the ferroelectric capacitor at equal time intervals. From these measurements, the rate of leakage of hydrogen gas into the closed integrated circuit package is calculated. The measurements are used to calculate the rate of leakage of hydrogen gas into the closed integrated circuit package.

An outer perimeter of the bismuth oxide based ferroelectric layer of the ferroelectric capacitor is exposed to a surrounding region of the ferroelectric capacitor, within the closed integrated circuit package. Hydrogen gas can be absorbed by the exposed outer perimeter of the bismuth oxide based ferroelectric layer of the ferroelectric capacitor. The hydrogen gas can pass into the ferroelectric layer. The hydrogen gas will react with bismuth oxide of the ferroelectric layer. The hydrogen gas chemically reduces the bismuth oxide of the bismuth oxide based ferroelectric layer to bismuth metal. A rate of chemical reduction of the bismuth oxide based ferroelectric layer by the hydrogen gas is increased when the integrated circuit package is heated.

The bismuth oxide based ferroelectric layer, that is located in the disclosed ferroelectric capacitor, has bismuth based stoichiometry. An example of a bismuth oxide based ferroelectric layer that has a bismuth based stoichiometry, is a Bi2SrTa72Nb28O9 ferroelectric layer.

SUMMARY OF THE INVENTION

A ferroelectric capacitor circuit for sensing hydrogen gas comprising a closed integrated circuit package, a ferroelectric capacitor within the closed integrated circuit package, the ferroelectric capacitor comprising a bismuth oxide based ferroelectric layer between a first capacitor plate and a second capacitor plate, an outer perimeter of the bismuth oxide based ferroelectric layer being exposed within the closed integrated circuit package, the outer perimeter of the bismuth oxide based ferroelectric layer being able to absorb hydrogen gas that is within the closed integrated circuit package, absorbed hydrogen gas chemically reducing a portion of the bismuth oxide based ferroelectric layer into bismuth metal, the ferroelectric capacitor having a ferroelectric voltage, the ferroelectric voltage having a voltage strength, and means for measuring a decrease in the voltage strength of the ferroelectric voltage of the ferroelectric capacitor.

DESCRIPTION OF THE DRAWING

FIG. 1 is a perspective view of an open integrated circuit package, the integrated circuit package holding a ferroelectric capacitor and holding an integrated circuit.

FIG. 2 is a sectional view of the ferroelectric capacitor of FIG. 1.

DESCRIPTION OF THE PREFERRED EMBODIMENT

Figure 4:
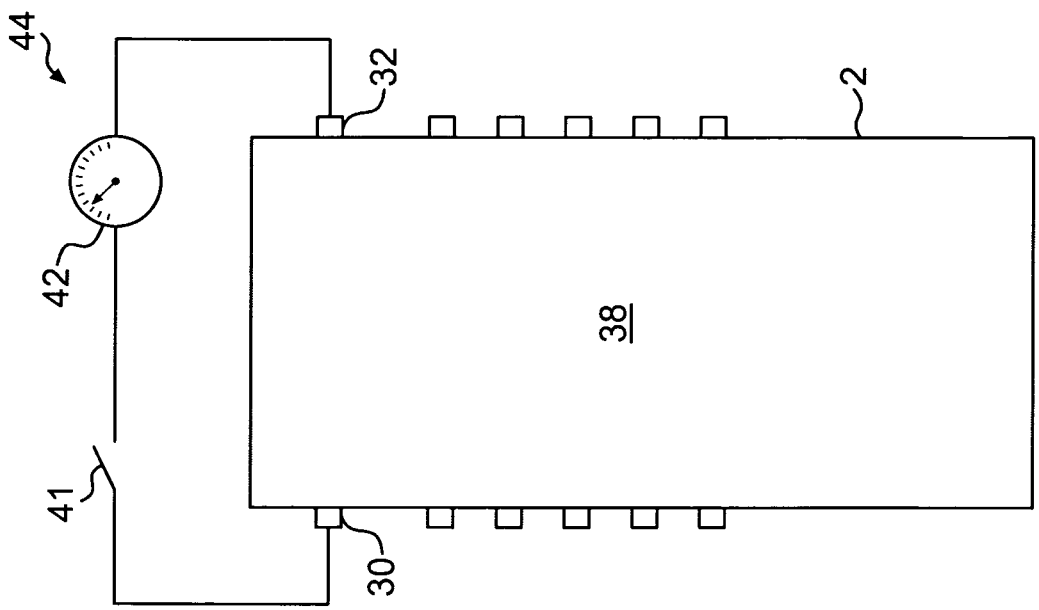
FIG. 4 is a schematic view of a ferroelectric capacitor circuit and a closed integrated circuit package.

FIG. 1 shows an open integrated circuit package 2. A ferroelectric capacitor 4 is located on an inner surface 14, shown in FIG. 2, of the open integrated circuit package 2. The ferroelectric capacitor 4 has a first capacitor plate 6, as shown in FIGS. 1 and 2. The capacitor 4 has a bismuth oxide based ferroelectric layer 8 and a second capacitor plate 10, as shown in FIG. 2. The capacitor plate 10 is built onto an insulator layer 12. The insulator layer 12 is built onto the inner surface 14 of the integrated circuit package 2.

In FIG. 2, the bismuth oxide based ferroelectric layer 8 is located between the first capacitor plate 6 and the second capacitor plate 10. The bismuth oxide based ferroelectric layer 8 is located on the second capacitor plate 10. An outer perimeter 13 of ferroelectric layer 8 of capacitor 4 is exposed. The perimeter 13 is exposed to an environment that is within the package 2, after the package 2 is closed. The perimeter 13 of the ferroelectric layer 8 will absorb hydrogen gas in the closed package, since the perimeter 13 of the ferroelectric layer 8 is not covered by either the capacitor plate 6 or the capacitor plate 10.

As shown in FIG. 2, a first lead 17 is connected to the first capacitor plate 6 of the capacitor 4. A second lead 18 is connected to the second capacitor plate 10 of capacitor 4. As shown in FIG. 1, the first lead 17 is connected to a first pin 30 of integrated circuit package 2. The second lead 18 is connected to a second pin 32 of integrated circuit package 2.

Figure 3:
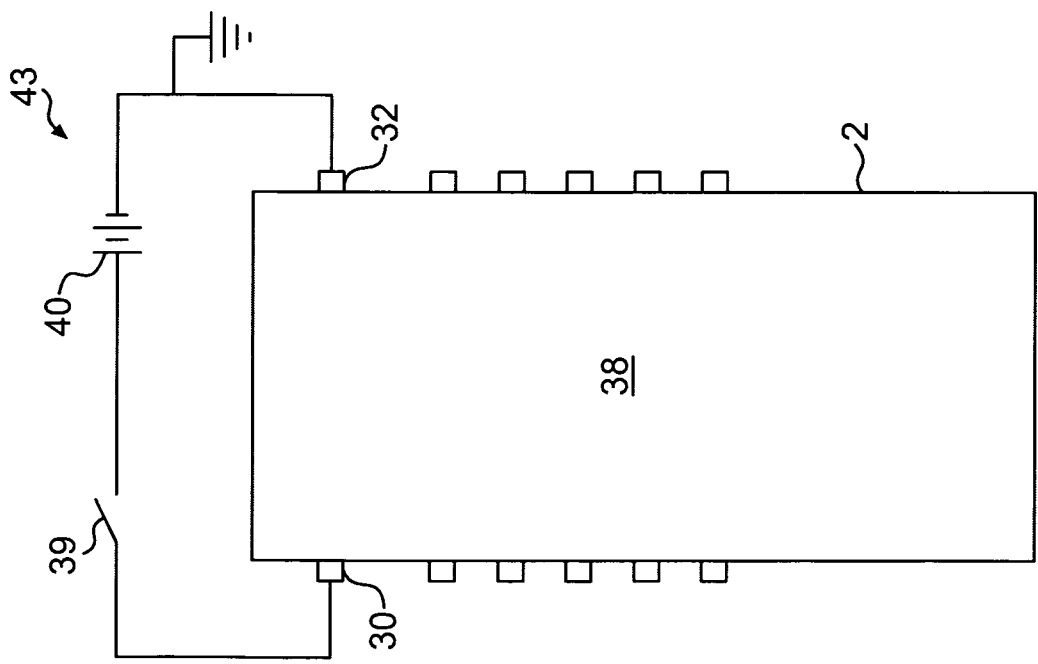
FIG. 3 is a schematic view of an energizing circuit and a closed integrated circuit package.

As shown in FIG. 1, an integrated circuit chip 16 is located on surface 14 of the integrated circuit package 2. The package 2 is closed by means of a lid 38, as shown in FIG. 3. The ferroelectric capacitor 4 is used in the closed integrated circuit package 4 to sense for any hydrogen gas that leaks into the closed integrated circuit package. The ferroelectric capacitor 4 can be used to determine whether or not hydrogen gas is leaking into closed package 2, to attack the integrated circuit chip 16.

The lid 38, as shown in FIG. 3, is used to close the integrated circuit package 2, in an attempt to completely seal the integrated circuit package 2 from an external environment to the integrated circuit package 2, including sealing the package 2 from environmental gases, such as hydrogen gas. However, the cover 38 might not provide a complete seal for package 2.

FIG. 3 shows an energizing circuit 43 for placing a ferroelectric voltage into the ferroelectric capacitor 4. As shown in FIG. 3, pin 30 is connected through a switch 39 to a positive 5 volt terminal of voltage source 40. Pin 32 is connected to a grounded negative terminal of voltage source 40. The bismuth oxide based ferroelectric layer 8 of the ferroelectric capacitor 4 is placed in a ferroelectric state by creating a 5 volt difference between capacitor plate 6 and capacitor plate 10. A 5 volt voltage difference is applied across pins 30 and 32 for 1 second by closing switch 39. The bismuth oxide ferroelectric layer 8 is thus placed at a ferroelectric voltage that has a 5 volt voltage strength, by closing switch 39 for 1 second.

The 5 volt voltage strength of the ferroelectric voltage on the bismuth oxide based ferroelectric layer 8 of the ferroelectric capacitor 4 will decrease as hydrogen gas migrates into the bismuth oxide ferroelectric layer 8, even though package 2 has been apparently sealed by means of the lid 38.

FIG. 4 shows a ferroelectric capacitor circuit 44 for sensing the voltage strength of the ferroelectric voltage in the ferroelectric capacitor 4, after the ferroelectric capacitor 4 has been given a ferroelectric voltage, as shown in FIG. 3. The voltage strength of the ferroelectric voltage of ferroelectric capacitor 4 is measured at two selected times over a selected time span. Switch 41 is closed at these two times and the voltage strength is measures by an electrometer 42. Voltage strengths of the ferroelectric layer 8 of ferroelectric capacitor 4 are measured at a beginning and end of the selected time span. A rate of decrease in voltage strength of a ferroelectric voltage in layer 8 is calculated. Such a rate of decrease is due to gradual degradation of the ferroelectric layer 8, by hydrogen gas. Again, the rate of decrease in the voltage strength is calculated. The rate of decrease of the voltage strength in capacitor 4 is proportional to a rate of absorption of hydrogen gas into the ferroelectric capacitor and thus into the interior of the integrated circuit package 2. The rate of absorption of hydrogen gas into the interior of the integrated circuit package 2 is thus detected and measured by ferroelectric capacitor circuit 44.

The bismuth oxide based ferroelectric layer 8 is a Bi2SrTa72Nb28O9 ferroelectric layer. Alternately, the bismuth oxide based ferroelectric layer 8 can be a PbBi2Nb2O9 ferroelectric layer.

The bismuth oxide based ferroelectric layer 8 will degrade when hydrogen gas leaks into a nominally hermetically sealed integrated circuit package 2. Degradation is due to the presence of hydrogen gas in the integrated circuit package 2.

The voltage strength of the bismuth oxide based ferroelectric layer 8 of ferroelectric capacitor 4 is probed using electrometer 42, as shown in FIG. 4, in order to sense the voltage strength in capacitor 4 and thus measure the amount of voltage strength degradation and physical degradation of the ferroelectric layer 8. The electrometer 42 measures voltage strengths in the ferroelectric layer 8 over time.

The ferroelectric layer 8 becomes more conductive as the bismuth oxide is chemically reduced by hydrogen gas, into bismuth metal. A 125 degree centigrade anneal of bismuth oxide in a 0.1% hydrogen atmosphere yields a very strongly conductive bismuth metal. 125 degree centigrade anneal processing of closed integrated circuit package 2 in a 0.1% hydrogen atmosphere, for processing times of 12 hours to 48 hours, significantly degrades the voltage strength in capacitor 4. Further, the conductivity of the ferroelectric layer 8 of the ferroelectric capacitor 4 is increased during the latter anneal processing.

The ferroelectric capacitor 4 is a ferroelectric memory device. Such a ferroelectric memory device is described and discussed in U.S. Pat. No. 6,203,869 issued Mar. 20, 2001. The teachings of U.S. Pat. No. 6,203,869 are incorporated herein by reference.

While the present invention has been disclosed in connection with the preferred embodiment thereof, it should be understood that there are other embodiments which fall within the spirit and scope of the invention as defined by the following claims.

What is claimed is:

1. A ferroelectric capacitor circuit for sensing hydrogen gas, comprising:
 (a) a closed integrated circuit package;
 (b) a ferroelectric capacitor within the closed integrated circuit package, the ferroelectric capacitor comprising a bismuth oxide based ferroelectric layer between a first capacitor plate and a second capacitor plate, an outer perimeter of the bismuth oxide based ferroelectric layer being exposed within the closed integrated circuit package, the outer perimeter of the bismuth oxide based ferroelectric layer being able to absorb hydrogen gas that is within the closed integrated circuit package, absorbed hydrogen gas chemically reducing a portion of the bismuth oxide based ferroelectric layer into bismuth metal, the ferroelectric capacitor having a stored ferroelectric voltage, the stored ferroelectric voltage having a voltage strength;
 (c) an electrometer for measuring a decrease in the voltage strength of the stored ferroelectric voltage of the ferroelectric capacitor; and
 (d) a DC voltage source for storing the stored ferroelectric voltage in the ferroelectric capacitor.

2. A ferroelectric capacitor circuit for sensing hydrogen gas, comprising:
 (a) a closed integrated circuit package;
 (b) a ferroelectric capacitor within the closed integrated circuit package, the ferroelectric capacitor comprising a bismuth oxide based ferroelectric layer between a first capacitor plate and a second capacitor plate, an outer perimeter of the bismuth oxide based ferroelectric layer being exposed within the closed integrated circuit package, the outer perimeter of the bismuth oxide based ferroelectric layer being able to absorb hydrogen gas that is within the closed integrated circuit package, absorbed hydrogen gas chemically reducing a portion of the bismuth oxide based ferroelectric layer into bismuth metal, the ferroelectric capacitor having a ferroelectric voltage, the ferroelectric voltage having a voltage strength, wherein the bismuth oxide based ferroelectric layer is a $Bi_2SrTa_{72}Nb_{28}O_9$ ferroelectric layer; and (c) means for measuring a decrease in the voltage strength of the ferroelectric voltage of the ferroelectric capacitor.

3. A ferroelectric capacitor circuit for sensing hydrogen gas, comprising:

(a) a closed integrated circuit package;

(b) a ferroelectric capacitor within the closed integrated circuit package, the ferroelectric capacitor comprising a $Bi_2SrTa_{72}Nb_{28}O_9$ ferroelectric layer between a first capacitor plate and a second capacitor plate, an outer perimeter of the bismuth oxide based ferroelectric layer being exposed within the closed integrated circuit package, the outer perimeter of the bismuth oxide based ferroelectric layer being able to absorb hydrogen gas that is within the closed integrated circuit package, absorbed hydrogen gas chemically reducing a portion of the bismuth oxide based ferroelectric layer into bismuth metal, the ferroelectric capacitor having a ferroelectric voltage, the ferroelectric voltage having a voltage strength; and (c) means for measuring a decrease in the voltage strength of the ferroelectric voltage of the ferroelectric capacitor.

4. A method for sensing hydrogen gas in an environment, comprising:

(a) placing a ferroelectric capacitor in the environment, the ferroelectric capacitor comprising a bismuth oxide based ferroelectric layer between a first capacitor plate and a second capacitor plate, an outer perimeter of the bismuth oxide based ferroelectric layer being exposed to the environment, the outer perimeter of the bismuth oxide based ferroelectric layer being able to absorb hydrogen gas that is in the environment, absorbed hydrogen gas chemically reducing a portion of the bismuth oxide based ferroelectric layer into bismuth metal;

(b) giving the ferroelectric capacitor a particular ferroelectric voltage; and (c) measuring voltage strengths of the ferroelectric voltage of the ferroelectric capacitor over time, to detect the chemical reduction of the bismuth oxide based ferroelectric layer into bismuth metal by the hydrogen gas.

* * * * *